United States Patent [19]

Badylak et al.

[11] Patent Number: 5,641,518
[45] Date of Patent: Jun. 24, 1997

[54] METHOD OF REPAIRING BONE TISSUE

[75] Inventors: Stephen F. Badylak, W. Lafayette; Sherry Voytik, Lafayette, both of Ind.

[73] Assignees: Purdue Research Foundation, West Lafayette; Methodist Hospital of Indiana, Inc., Indianapolis, both of Ind.

[21] Appl. No.: 386,432

[22] Filed: Feb. 10, 1995

Related U.S. Application Data

[63] Continuation-in-part of Ser. No. 343,204, Nov. 22, 1994, Pat. No. 5,516,533, which is a continuation of Ser. No. 176,565, Jan. 3, 1994, abandoned, which is a continuation of Ser. No. 976,156, Nov. 13, 1992, Pat. No. 5,275,826.

[51] Int. Cl.$^6$ ................................................ A61K 35/38
[52] U.S. Cl. ........................... 424/551; 623/11; 623/16
[58] Field of Search .......................... 424/551; 623/11, 623/16

[56] References Cited

U.S. PATENT DOCUMENTS

| | | | |
|---|---|---|---|
| 2,987,062 | 6/1961 | Ellison | 606/74 |
| 4,263,185 | 4/1981 | Belykh et al. | 62/79 |
| 4,365,357 | 12/1982 | Draenert | 623/16 |
| 4,902,508 | 2/1990 | Badylak et al. | 424/551 |
| 4,956,178 | 9/1990 | Badylak et al. | 424/551 |
| 5,037,950 | 8/1991 | Bezwada et al. | 528/354 |
| 5,129,906 | 7/1992 | Ross et al. | 606/77 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,372,821 | 12/1994 | Badylak et al. | 424/551 |

FOREIGN PATENT DOCUMENTS

| | | |
|---|---|---|
| 141094 | 4/1971 | Czechoslovakia . |
| PCT/US94/ 09979 | 3/1995 | WIPO . |

OTHER PUBLICATIONS

*A Simple Method of Arthrodesis of the First Metatarsophalangeal Joint.* G.S. Chana, T.A. Andrew, C.P. Cotterill. *The Journal of Bone and Joint Surgery,* British vol. 66–B, No. 5, pp. 703–705, 1994.

Primary Examiner—Jean C. Witz
Attorney, Agent, or Firm—Barnes & Thornburg

[57] ABSTRACT

A method for repairing damaged or diseased bone is described. The method comprises the step of implanting into the damaged or diseased region a bone graft composition in powder form, the composition comprising the tunica submucosa delaminated from the tunica muscularis and at least the luminal portion of the tunica mucosa of a segment of vertebrate intestine.

4 Claims, No Drawings

METHOD OF REPAIRING BONE TISSUE

This is a continuation-in-part application of U.S. application Ser. No. 08/343,204, filed Nov. 22, 1994, now U.S. Pat. No. 5,516,533, which is a continuation of U.S. application Ser. No. 08/176,565, filed Jan. 3, 1994, now abandoned, which is a continuation of U.S. application Ser. No. 07/976,156, filed Nov. 13, 1992, issued as U.S. Pat. No. 5,275,826 on Jan. 4, 1994.

BACKGROUND AND SUMMARY OF THE INVENTION

The present invention relates to a bone graft composition in powder form and methods for its preparation and use. More particularly, the present invention is directed to non-immunogenic bone graft compositions in powder form comprising the tunica submucosa delaminated from the tunica muscularis and at least the luminal portion of the tunica mucosa of a segment of warm-blooded vertebrate intestine. Upon deposition into a damaged or defective region of bony tissue, the present bone graft powder compositions promote growth of endogenous tissue to repair the damaged or defective region.

It has been reported that compositions comprising the tunica submucosa and the basilar portions of the tunica mucosa of the intestine of warm-blooded vertebrates can be used as tissue graft materials in sheet form. See U.S. Pat. No. 4,902,508. The preferred compositions described and claimed in that patent are characterized by excellent mechanical properties, including high compliance, a high burst pressure point, and an effective porosity index which allowed such compositions to be used beneficially for vascular graft constructs. The graft materials disclosed in that patent are also useful in tendon and ligament replacement applications. When used in such applications the preferred graft constructs appear to serve as a matrix for the regrowth of the tissues replaced by the graft constructs.

Furthermore, it has been discovered that intestinal submucosa can be fluidized by comminuting and/or protease digestion, without loss of its apparent biotropic properties, for use in less invasive methods of administration (e.g., injection or topical) to host tissues in need of repair. See U.S. Pat. No. 5,275,826. Fluidized comminuted intestinal tissue comprising tunica submucosa has previously been successfully used to remodel damaged ligaments and tendons. Common events to this remodeling process include: widespread and very rapid neovascularization, proliferation of granulation mesenchymal cells, biodegradation of implanted SIS material, and lack of immune rejection.

The present application discloses methods for inducing the repair of bone in a warm-blooded vertebrates. The method comprising the step of implanting a bone graft composition, in powder form, into a site in need of repair under conditions conducive to the proliferation of endogenous tissues. The powder bone graft composition is formed from intestinal tissue of a warm-blooded vertebrate, the intestinal tissue comprising the tunica submucosa delaminated from the tunica muscularis and at least the luminal portion of the tunica mucosa, or a protease digest thereof.

Approximately 300,000 bone grafting and fracture repair procedures are performed each year in the United States. The market potential of an inexpensive, readily prepared and easily maintained bone graft material is estimated to be greater than 300 million dollars. Such biomaterials may be used to effectively repair fractures, craniofacial defects, periodontal defects, arthrodesis, and skeletal reconstruction following secondary bone loss to infection or neoplasm.

Currently, fresh autologous bone is the most effective bone graft material available. However, there are several disadvantages associated with the use of bone autografts including limited supply, the need for additional surgical procedures, and added morbidity associated with its harvest. Allogeneic bone grafts are also clinically used, but such graft compositions have serious shortcomings associated with their use, including the limited availability of cadaver bone, the quality of the banked bone, and the potential spread of human disease.

Ceramics, such as hydroxyapatite or tricalcium phosphate are also being investigated, but these materials are only osteoconductive rather than osteoinductive: i.e. new bone is generally only formed adjacent to the implant and the normal bone. More recently, a material known as Collagraft has been investigated as a potential bone graft material. It is a composite of bovine collagen, hydroxyapatite/tricalcium phosphate fibrillae ceramic, and bone marrow (aspirated from the iliac crest of the patient). The disadvantage of Collagraft is it lacks structural strength, and therefore is not useful in situations where cortical grafting is needed.

Because of the disadvantages associated with current bone repair therapeutic strategies, there is a strong need for alternative bone graft materials. It has been previously reported that compositions comprising tunica submucosa and basilar portions of the tunica mucosa of vertebrate intestine can be used as tissue graft materials which induce the growth of endogenous tissues. Applicants have discovered that powder forms of intestinal tissue comprising tunica submucosa and basilar portions of the tunica mucosa retain their biotropic properties and can be used as a bone graft material. As an alternative bone graft material, the present powder forms serve as a plentiful biological by-product that is inexpensive, readily prepared and easily maintained. This material induces and/or supports the regeneration of bony skeletal tissue, and preliminary results suggest that the structural and mechanical integrity of the grafted area is at least equivalent to that of the preexisting bone.

According to the present invention, a non-immunogenic bone graft composition in powder form is provided. In one embodiment the composition comprises lyophilized comminuted large or small intestinal tissue comprising the tunica submucosa delaminated from the tunica muscularis and at least the luminal portion of the tunica mucosa. In another aspect of the invention, there is provided a bone graft composition comprising lyophilized protease-digested intestinal tissue comprising the tunica submucosa delaminated from the tunica muscularis and at least the luminal portion of the tunica mucosa.

The described formulations have a variety of clinical uses in orthopedic surgery such as augmenting bony fusions, aiding in the repair of high-risk fractures, filling or bridging of bone defects, and assisting the attachment of metal or plastic prosthetic devices. In addition, they may be valuable in the treatment of periodontal disease, and in other tooth repair processes.

Furthermore, pharmaceuticals and bioactive agents can be admixed, coupled, or complexed with the bone graft compositions of this invention to create a composition for treating bone disorders locally.

In a preferred embodiment, the bone graft compositions described in this application are used advantageously in a method for inducing the repair of bone in a warm-blooded vertebrate. The method comprises the step of implanting a bone graft composition in powder form into the damaged or defective region, wherein the bone graft composition comprises the tunica submucosa and the basilar portions of the tunica mucosa of a segment of vertebrate intestine or a protease digest thereof. Most preferably the intestinal tissue consists essentially of the tunica submucosa, the muscularis mucosa and the stratum compactum of the tunica mucosa of warm-blooded intestinal tissue.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE PREFERRED EMBODIMENTS

One preferred starting material for bone graft compositions in accordance with the present invention comprises submucosal tissue of a warm-blooded vertebrate. This submucosal tissue can be obtained from various sources, including intestinal tissue harvested from animals raised for meat production, including, for example, pigs, cattle and sheep or other warm-blooded vertebrates.

The submucosal tissue used in accordance with the present invention is preferably derived from the intestines, more preferably the small intestine, of a warm-blooded vertebrate. Intestinal submucosal tissue may include basilar portions of the tunica mucosa. One preferred material for preparation of the present compositions comprises the tunica submucosa along with the lamina muscularis mucosa and the stratum compactum of a segment of small intestine, delaminated from the tunica muscularis and the luminal portion of the tunica mucosa of said segment. Such material is generally referred to herein as intestinal submucosa.

The preparation of intestinal submucosa from a segment of small intestine is detailed in U.S. Pat. No. 4,902,508, the disclosure of which is expressly incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically the intestinal submucosa is rinsed with saline and optionally stored in a frozen hydrated state until use as described below.

In one preferred embodiment a bone graft composition in accordance with the present invention is prepared from intestinal tissue comprising the tunica submucosa delaminated from the tunica muscularis and the luminal portion of the tunica mucosa of vertebrate intestine. Alternatively the bone graft composition in powder form can be prepared from fluidized intestinal submucosa.

Fluidized intestinal submucosa is prepared as described in U.S. Pat. No. 5,275,826 the disclosure of which is expressly incorporated herein by reference. The intestinal submucosa starting material is comminuted by tearing, cutting, grinding, shearing and the like. Grinding the intestinal submucosa in a frozen or freeze-dried state is preferred although good results can be obtained as well by subjecting a suspension of submucosa pieces to treatment in a high speed (high shear) blender and dewatering, if necessary, by centrifuging and decanting excess water. The comminuted tissue can be solubilized by proteolytic digestion of the submucosa with a protease, such as trypsin or pepsin, at an acidic pH for a period of time sufficient to solubilize said tissue and form a substantially homogeneous solution.

In one embodiment a powder form of warm blooded vertebrate intestinal tissue comprising the tunica submucosa delaminated from the tunica muscularis and the luminal portion of the tunica mucosa of vertebrate intestine is prepared by pulverizing the intestinal submucosa tissue under liquid nitrogen to produce particles ranging in size from 0.1 to 1 $m^2$. The particulate is then lyophilized overnight and sterilized to form a solid substantially anhydrous particulate composite.

In an alternative embodiment, a bone graft composition in powder form is formed from fluidized intestinal submucosa. In this embodiment, the prepared suspensions and solutions of comminuted intestinal submucosa are dried to form the powderized compositions of the present invention.

The present bone graft compositions can be sterilized using art-recognized sterilization techniques including glutaraldehyde tanning with glutaraldehyde, formaldehyde tanning at acidic pH, propylene oxide treatment, gas plasma sterilization, gamma radiation, electron beam and peracetic acid sterilization. The tissues can be sterilized during the preparation of the bone graft composition, or subsequent to the formation of the composition but prior to implantation into a host. A sterilization technique which does not significantly weaken the mechanical strength, structure and biotropic properties of the graft is preferably used. For instance, it is believed that strong gamma radiation may cause loss of strength in the graft material. Because one of the most attractive features of the bone graft compositions is their ability to induce host-remodelling responses, it is desirable not to use a sterilization approach which will detract from that property. Preferred sterilization techniques include exposing the graft to peracetic acid, 1–4 Mrads gamma irradiation, more preferably 1–2.5 Mrads of gamma irradiation, and gas plasma sterilization; peracetic acid sterilization being the most preferred method. Typically, the submucosal tissue is subjected to two or more sterilization processes. After the submucosal tissue has been sterilized, the submucosal tissue may be wrapped in a plastic or foil wrap and sterilized again using electron beam or gamma irradiation sterilization techniques.

Bone graft compositions in accordance with the present invention can be utilized in a method for inducing the repair of a damaged or defective region of a warm-blooded vertebrate's bony tissue. The method comprises the step of implanting the bone graft composition into the damaged or diseased region under conditions conducive to proliferation of endogenous tissues.

In one embodiment of the present invention, lyophilized bone graft compositions can be used as an implantable heterograft for bone tissues in need of repair or augmentation, most typically to correct trauma or disease-induced tissue defects. Advantageously the powder form of intestinal submucosa can be compressed into a variety of shapes that hold their shaped form for implantation into a patient. In this manner, the powder form can be compressed into a construct shaped to fit the area targeted for endogenous bone formation. Optimally the compressed powder bone graft will maintain its general shape after implantation during replacement of the graft construct with endogenous tissues. Additional support materials may be combined with the bone graft powder prior to compressing the powder composition into its desired shape. For example hydroxyapatite and/or other biocompatible calcium containing minerals can be combined with the bone graft in powder form to give additional structural support for the remodeled replacement tissue. Alternatively the powder bone graft composition can be pressed onto an existing structure or prosthesis to form a bone graft layer on the structure prior to implantation of the structure/prothesis into a patient.

In addition, tricalcium phosphate or other suitable physiological mineral sources can be combined with the bone graft compositions to assist in repair of damaged or diseased bone. In preferred embodiments, physiological compatible mineral may comprise up to 80% of the bone graft composition. Preferably the physiological compatible mineral comprises about 5% to about 50% of the bone graft composition, and most preferably comprises about 5% to 30% of the bone graft composition. In another embodiment of the present invention, pharmaceuticals and bioactive agents are admixed with the powder intestinal submucosal graft material to create a delivery system for the local treatment of bone disorders or diseases. In particular, the bone graft compositions of the present invention can be combined with an effective amount of bioactive ingredients, such as antibiotics, chemotherapeutic agents, growth factors, antigens, antibodies, enzymes or hormones.

For example, a tissue graft composition comprising intestinal submucosal material and an antibiotic may be useful in the treatment of osteomyelitis, thereby reducing the need for and risk of parenteral antibiotics. In addition, a tissue graft composition comprising intestinal submucosal material and an antineoplastic agent could be used for the local treatment of bone neoplasm; and finally, a tissue graft composition comprising intestinal submucosal material and an osteogenic or other growth factor (e.g., osteogenin, bone morphogenetic protein, parathyroid hormone, and TGFβ) could be useful to accelerate the repair of skeletal defects as occurs with excessive trauma and with skeletal deficiency disorders such as osteogenesis imperfecta and osteoporosis.

EXAMPLE 1

Bone Graft Composition in Powder Form

Small intestine tissue comprising tunica submucosa and the basilar portions of vertebrate intestine is minced or chopped into arbitrarily small pieces using tissue scissors, a single-edged razor blade, or other appropriate cutting implement. The tissue specimen are then are placed in a flat bottom stainless steel container and liquid nitrogen is introduced into the container to freeze the tissue specimen to prepare them for comminuting.

The frozen specimen are then comminuted to form a coarse powder. Such processing can be carried out, for example, with a manual arbor press with a cylindrical brass ingot placed on top of the frozen specimen. The ingot serves as an interface between the specimen and the arbor of the press. It is typically necessary to add liquid nitrogen periodically to the specimen to keep them frozen.

Other methods for comminuting small intestine tissue comprising submucosa tissue may be utilized to produce a bone graft composition in powder form, usable in accordance with the present invention. For example, small intestine tissue comprising submucosa tissue can be freeze-dried and then ground. Alternatively, small intestine tissue comprising submucosa tissue can be processed in a high shear blender to produce, upon dewatering and drying, a bone graft composition in powder form. Further grinding of the submucosa powder using a pre-chilled mortar and pestle can be used to produce a consistent, more finely divided product. Again, liquid nitrogen is used as needed to maintain solid frozen particles during final grinding.

EXAMPLE 2

Solubilized Bone Graft Composition in Powder Form

Bone graft compositions comprising comminuted intestinal submucosa can be solubilized to form a substantially homogeneous solution by digesting the composition with a protease. In one preferred embodiment, comminuted intestinal submucosa in powder form (prepared as describe in example 1) is sifted through a wire mesh into a vessel and resuspended. The powder is then digested with 1 mg/ml of pepsin (Sigma Chemical Co., St. Louis, Mo.) in 0.1M acetic acid, adjusted to pH 2.5 with HCl, over a 48 hour period at room temperature. The reaction medium is neutralized with sodium hydroxide to inactivate the peptic activity. The solubilized submucosa is then concentrated by salt precipitation of the solution and separated for further purification and/or freeze drying to form a protease solubilized intestinal submucosa in powder form.

EXAMPLE 3

Applications

Two different bone graft compositions comprising intestinal submucosa were investigated for their induction of endogenous growth of bone tissue. One formulation consists of submucosa in its natural hydrated state and the other represents intestinal submucosa as a lyophilized particulate.

To determine the osteogenic ability of intestinal submucosa, applicants used a well established animal model. The model involved formation of circular defects (8-mm diameter) in the parietal bones of adult (greater than 6 mos. of age) Sprague Dawley rats. The defect is of a critical size such that the intraosseous wound would not heal by bone formation during the lifetime of the animal. Various formulations of rat or porcine small intestinal submucosa were placed on the dura within the defect margins. Additional rats in which no material or demineralized allogeneic bone particles were placed in the defect area served as negative and positive controls, respectively. The periosteal and skin layers were then sutured closed and the animals recovered for periods of 2 weeks to 1 year. At necropsy, the calvaria were grossly examined and radiomorphometry was used to measure radiopacity of skeletal defects. The calvaria were then harvested, fixed, sectioned, and stained for histological evaluation.

Intestinal submucosa in its natural hydrated state was prepared from porcine and rat small intestine as previously described by in U.S. Pat. No. 4,902,508, the disclosure of which is expressly incorporated herein by reference. The material was rinsed in phosphate buffered solution containing an antibiotic (gentamicin sulfate) and a protease inhibitor (phenylmethylsulfonyl fluoride) and then sterilized using peracetic acid, gamma-irradiation, and other techniques. Prior to implantation, the material was minced into 1×1 mm$^2$ pieces and rinsed in sterile saline.

Intestinal submucosa as a dehydrated particulate was prepared by pulverizing intestinal submucosa under liquid nitrogen to achieve particles which ranged from 0.1 to 1 mm$^2$ in size. The particulate was then lyophilized overnight and then sterilized to form a solid anhydrous particulate composite.

When no material is applied to the defect area, new bone growth was limited to the defect margins, whereas the central portion of the defect showed a disorganized fibrous connective tissue matrix. Incomplete healing (less than 10%) of the defect remained evident at 12 weeks following surgery.

Four weeks following implantation of demineralized bone particles, spicules of new bone growth were evident throughout the defect area. By 8 weeks, bridges of new woven bone were evident between demineralized bone particles and between the edges of the defect and demineralized bone particles. Based on radiographic data approximately 70–80% of the original defect area was filled by new bone. Thereafter, new bone growth appeared to increase in density and level of maturation such that none of the original defect area remained.

Studies involving various formulations of intestinal submucosa indicated that after four weeks following implantation, islands of new bone formed at the edges of the defect and throughout the defect area. By eight weeks, the new bone growth increased in density and level of maturation such that the defect margins were bridged with new bone: the new bone occupying about 70–80% of the original defect area. The new bone was effectively fused with the old bone flanking the defect.

Based on the currently available data, there are no observable differences between the effectiveness of intestinal submucosa in its natural hydrated state as compared to intestinal submucosa as a lyophilized particulate when used to induce new bone formation. At early time points (4 weeks following implantation), it appears that both are effective at inducing osteogenic activity. Additionally, it is apparent that intestinal submucosa in its natural hydrated state and as a lyophilized particulate induced growth of new bone more efficiently and at a faster rate than currently used therapeutic strategies. The resultant new bone growth induced by the intestinal submucosa was more homogenous than that observed in the positive control animals.

Advantageously, lyophilized particulate compositions of the present invention can be molded, pressed, and contoured, for example, to fit a bone defect. In addition, composites involving intestinal submucosa and various other materials (e.g., hydroxyapatite, tricalcium phosphate, etc.) may be formed and useful for tissue repair.

The lyophilized submucosa compositions of this invention find wide application both in bone tissue replacement and repair. Bone graft compositions used in accordance with the present disclosed method can induce regrowth of natural connective tissue or bone in an area of an existent defect. Damaged or defective regions of bone can be repaired by contacting the damaged or defective region with a bone graft composition comprising intestinal submucosa.

Perhaps the most remarkable aspect of the compositions of the present invention is their ability to induce regrowth of natural bone tissue in an affected area. By contacting a damaged or defective region of bony tissue with an effective amount of the present lyophilized intestinal submucosa compositions, one can induce natural bone growth and repair of the damaged or defective region.

Although the invention has been described in detail with reference to certain preferred embodiments, variations and modifications exist within the scope and spirit of the invention as described and defined in the following claims.

We claim:

1. A method for inducing the repair of bone in a warm-blooded vertebrate, said method comprising the step of implanting an effective amount of a biodegradable bone graft construct into a site in said vertebrate in need of repair, said bone graft construct consisting essentially of intestinal submucosal tissue of a warm-blooded vertebrate or a digest thereof in powder form compressed into a pre-determined three-dimensional shape prior to implantation, wherein the compressed powder bone graft maintains its general shape after implantation during the replacement of the graft construct with endogenous tissues.

2. A method for including the repair of bone in a warm-blooded vertebrate, said method comprising the step of implanting an effective amount of a biodegradable bone graft construct into a site in said vertebrate in need of repair, said bone graft construct consisting essentially of intestinal submucosal tissue of a warm-blooded vertebrate or a digest thereof in powder form and an added bioactive agent selected from the group consisting of physiological compatible minerals, growth factors, antibiotics, chemotherapeutic agents, antigens, antibodies, enzymes and hormones, wherein said powder bone graft is compressed into a pre-determined three-dimensional shape prior to implantation, and the compressed powder bone graft maintains its general shape after implantation during the replacement of the graft construct with endogenous tissues.

3. A method for inducing the repair of bony tissue, said method comprising the step of implanting an effective amount of a biodegradable bone graft construct into a site in said vertebrate in need of repair, said bone graft construct formed by compressing intestinal submucosal tissue or a digest thereof in powder form into a pre-determined three-dimensional shape prior to implantation said intestinal submucosal tissue comprising the tunica submucosa delaminated from the tunica muscularis and the luminal portion of the tunica mucosa of a warm-blooded vertebrate wherein the compressed powder bone graft maintains its general shape after implantation during the replacement of the graft construct with endogenous tissues.

4. A method for inducing the repair of bony tissue, said method comprising the step of implanting an effective amount of a biodegradable bone graft construct into a site of said vertebrate in need of repair, said bone craft construct formed by compressing a composition comprising intestinal submucosal tissue or a digest thereof in powder form and an added bioactive agent into a pre-determined three-dimensional shade prior to implantation, wherein said intestinal submucosal tissue comprises the tunica submucosa delaminated from the tunica muscularis and the luminal portion of the tunica mucosa of a warm-blooded vertebrate, said bioactive agent is selected from the group consisting of physiological compatible minerals, growth factors, antibiotics, chemotherapeutic agents, antigens, antibodies, enzymes and hormones, and said compressed powder bone graft maintains its general shape after implantation during the replacement of the graft construct with endogenous tissues.

* * * * *